US009115078B2

(12) United States Patent
Smith et al.

(10) Patent No.: US 9,115,078 B2
(45) Date of Patent: Aug. 25, 2015

(54) COMPOSITIONS FOR IMPROVING THE QUALITY OF THE MEIBUM COMPOSITION OF INFLAMED OR DYSFUNCTIONAL MEIBOMIAN GLANDS

(75) Inventors: S. Gregory Smith, Yorklyn, DE (US); Michael B. Gross, Plymouth Meeting, PA (US); Olav E. Sandnes, Mt. Bethel, PA (US)

(73) Assignee: Physicians Recommended Nutriceuticals, LLC, Plymouth Meeting, PA (US)

( * ) Notice: Subject to any disclaimer, the term of this patent is extended or adjusted under 35 U.S.C. 154(b) by 32 days.

(21) Appl. No.: 13/507,673

(22) Filed: Jul. 18, 2012

(65) Prior Publication Data

US 2013/0065867 A1     Mar. 14, 2013

Related U.S. Application Data

(60) Provisional application No. 61/572,574, filed on Jul. 18, 2011.

(51) Int. Cl.
*A61K 31/225* (2006.01)
*A61K 31/20* (2006.01)
*C07C 69/587* (2006.01)
*A61K 31/593* (2006.01)
*A61K 31/202* (2006.01)
*A61K 31/231* (2006.01)

(52) U.S. Cl.
CPC ............. *C07C 69/587* (2013.01); *A61K 31/202* (2013.01); *A61K 31/231* (2013.01); *A61K 31/593* (2013.01)

(58) Field of Classification Search
CPC ... A61K 31/231; A61K 31/232; C07D 69/587
USPC .................................. 514/547, 560, 167, 224
See application file for complete search history.

(56) References Cited

U.S. PATENT DOCUMENTS

| | | | |
|---|---|---|---|
| 6,353,022 B1 | 3/2002 | Schneider et al. | |
| 6,506,412 B2 | 1/2003 | Troyer et al. | |
| 6,566,398 B1 | 5/2003 | Ueno | |
| 6,649,195 B1 | 11/2003 | Gorsek | |
| 7,417,071 B2 | 8/2008 | Gandhi | |
| 2004/0076695 A1 | 4/2004 | Gilbard | |
| 2005/0147648 A1 | 7/2005 | Gierhart | |
| 2006/0127505 A1 | 6/2006 | Haines et al. | |
| 2007/0141170 A1 | 6/2007 | Lang | |
| 2008/0260859 A1* | 10/2008 | Claus-Herz et al. | 424/641 |
| 2009/0136445 A1 | 5/2009 | Wong et al. | |
| 2009/0226547 A1 | 9/2009 | Gilbard et al. | |
| 2010/0028459 A1 | 2/2010 | Kis | |
| 2010/0048705 A1 | 2/2010 | Smith et al. | |
| 2010/0068298 A1 | 3/2010 | Kis | |
| 2010/0093648 A1 | 4/2010 | Cruz | |
| 2010/0330171 A1 | 12/2010 | Gilbard et al. | |
| 2011/0111055 A1* | 5/2011 | Lang | 424/638 |
| 2012/0258168 A1* | 10/2012 | Montesinos | 424/455 |
| 2013/0011469 A1 | 1/2013 | Minatelli et al. | |
| 2014/0024625 A1* | 1/2014 | Smith et al. | 514/167 |

OTHER PUBLICATIONS

J.P. Schuchardt et al., Moderate doses of EPA and DHA from re-esterified triacylglycerols but not from ethyl-esters lower fasting serum triadyglycerols in statin-treated dyslipidemic subjects: Results from six month randomized controlled trial, plefa, vol. 85, Issue 6, pp. 381-386, Dec. 2011.
J. Neubronner et al., Enhanced increase of omega-3 index in response to long-term n-3 fatty acid supplementation from triacylglycerides verses ethyl esters, European Journal of Clinical Nutrition 65, pp. 247-254 (Feb. 2011), doi:10.1038/ejcn.2010.239.
Jadwiga C. Wojtowicz et al., Pilot, Prospective, Randomized, Double-masked, Placebo-controlled Clinical Trial of an Omega-3 Supplement for Dry Eye, Cornea, (2010).
J. Dyerbert et al., Bioavailability of marine n-3 fatty acid formulations, Prostaglandins Leukotrienes Essent. Fatty Acids (2010), doi: 10.1016/j.plefa.2010.06.007.
Robert S. Chapkin et al, Dietary docosahexaenoic and eicosapentaenoic acid: Emerging mediators of inflammation, Prostaglandins Leukotrienes Essent Fatty Acids (2009), doi:10.1016/j.plefa.2009.05.010.
J. Thomas Brenna et al, α-Linolenic acid supplementation and conversion to n-3 long-chain polyunsaturated fatty acids in humans, Prostaglandins Leukotrienes Essent. Fatty Acids (2009), doi:10.1016/j.plefa.2009.01.004.
Charles N. Serhan et al., Maresins: novel macrophage mediators with potent antiinflammatory and proresolving actions, J. Exxp. Med., vol. 206, No. 1 (2008).
Marian S Macsai, The Role of Omega-3 Dietary Supplementation in Blepharitis and Meibomian Gland Dysfunction (An AOS Thesis), Trans Am Ophthalmol Soc, vol. 106 (2008).
Igor A. Butovich et al., Lipids of human meibum: mass-spectrometric analysis and structural elucidation, Journal of Lipid Research, vol. 48 (2007).
Sullivan et al., Third International Conference on the Lacrimal Gland, Tear Film and Dry Eye Syndrome: Basic Science and Clinical Relevance, Maui, Hi., Nov. 15-18 (2000).
http://seniorjournal.com/NEWS/Nutrition-Vitamins/2007/7-05-14-Omega3FattyAcids.htm.
http://www.umm.edu/altmed/articles/macular-degeneration-000104.htm.

(Continued)

*Primary Examiner* — My-Chau T Tran
(74) *Attorney, Agent, or Firm* — Pierce IP Law PLLC

(57) ABSTRACT

This invention relates to methods for administering an effective amount of a dietary or nutritional supplement composition that effectively changes the quality of the meibum lipid composition of inflamed or dysfunctional meibomian glands so as to improve or increase tear break up time, reduce tear osmolarity, and elevate the omega-3 index, while reducing or eliminating the symptoms associated with dry eye or meibomianitis. The dietary or nutritional supplement composition administered to the patient suffering from inflamed or dysfunctional meibomian glands comprises an effective amount of omega-3 fatty acids.

20 Claims, No Drawings

(56) References Cited

OTHER PUBLICATIONS http://www.aboutomega3.com/omega_3_and_macular_degeneration_-_what_you_need_to_know.html.
http://www.medrounds.org/amd/2005/08/lutein-zeaxanthin-and-omega-3-poly.html.
http://www.futurepundit.com/archives/006299.html.
http://www.ncbi.nlm.nih.gov/pubmed/16815401.
http://ezinearticles.com/?Omega-3-Study-For-Macular-Degeneration&id=4312997.
http://www.emaxhealth.com/1275/96/34058/omega-3-helps-prevent-macular-degeneration.html.

* cited by examiner

COMPOSITIONS FOR IMPROVING THE QUALITY OF THE MEIBUM COMPOSITION OF INFLAMED OR DYSFUNCTIONAL MEIBOMIAN GLANDS

RELATED APPLICATION

This application claims the benefit of U.S. Provisional Patent Application Ser. No. 61/572,574, filed on Jul. 18, 2011 and entitled "COMPOSITIONS AND METHODS FOR USING SAME FOR TREATING POSTERIOR BLEPHARITIS."

BACKGROUND

1. The Field of the Invention

This invention relates to methods for improving and enhancing the lipid layer of the tear and increasing tear breakup time and elevating the omega-3 index in patients suffering from symptoms of posterior blepharitis and, more specifically, to methods for administering a supplementation of omega-3 fatty acids to normalize the oil production of the meibomian glands, thus normalizing the lipid layer of the tear.

2. The Background Art

Along the margin of the eyelids are a series of small sebaceous glands called meibomian glands. The meibomian glands create and distribute a supply of meibum, an oily substance, that makes up the lipid layer that helps keep the eye moist and protects the tear film from evaporation. There are approximately twenty-five meibomian glands on the upper eyelids and twenty-five glands on the lower eyelids. Upon blinking of the eye, the upper eyelid comes down, presses on the oily substance produced by the meibomian glands, and pulls a sheet of this oily substance upwards, thereby coating the tear layer beneath to keep it from evaporating. This oily substance or meibum (wherein lipids are a major component) created by the meibomian glands is therefore critical for healthy eyes and good vision.

Meibomianitis refers to inflammation or dysfunction of the meibomian glands. Inflammation of the meibomian glands may occur because of the production of meibum which is pro-inflammatory in nature due to an increased composition of omega-6 essential fatty acids. Secondarily, bacteria have been found to invade the meibomian glands and colonize there. Once inflamed, the meibomian glands generally will not produce the quantity and quality of oils that are necessary to properly lubricate the eye.

The volume of oil produced from inflamed meibomian glands tends to decrease and the oils that are produced become thicker, like toothpaste. These oils also become abnormal in their characteristics. Instead of spreading evenly across the aqueous layer, the oil coalesces leaving areas in which the aqueous can evaporate and other areas in which the oil now adheres to the cornea surface itself. This creates a dry spot on the cornea which the aqueous cannot penetrate. Such condition generally produces a foreign body sensation and if it persists may result in injury to the epithelium which is seen as corneal staining on examination. A reduction in oil production therefore inherently results in a quantitative decrease in the quality and quantity of the oily layer, thus causing tears to evaporate more rapidly. Because the thickened oil does not coat the eye properly, a person with inflamed meibomian glands may experience discomfort or problems with their eyes that may include, for example, but not by way of limitation: (1) dryness; (2) burning; (3) itching; (4) irritation and redness; (5) blurred vision; and/or (6) foreign body sensations.

This inflammatory process can also spread throughout the lid margin and spill over to involve the ocular surface resulting in significant ocular discomfort. Inflammation of the meibomian glands in the upper and lower lids can further lead to vascularization and fibrosis, causing stenosis and then closure of the meibomian gland orifices. Deprived of the meibum or lipids that inhibit evaporation, tear film evaporation will generally increase. Similarly, a deficiency in tear film generally results in irritation of the eye, but can also cause damage to the surface of the eye. As appreciated, an irregular oil pattern disrupts tears and allows for increased exposure of the aqueous layer to the atmosphere and the increased evaporation of the aqueous. Unfortunately, this inflamed condition of the meibomian glands has often been found to be chronic.

Some of the treatments for meibomianitis that have been contemplated by those skilled in the art include: (1) the application of artificial tears; (2) cleaning the affected eyelid margins with a gentle baby shampoo; and (3) applying warm and moist compresses 5-10 minutes two to three times per day in an effort to promote normal eyelid glandular function. A physician may also prescribe a topical and/or oral antibiotic such as, for example, tetracycline, erythromycin, or doxycycline, to help eradicate the bacteria found in the glands and to facilitate a breakdown in the thickened lipid secretions from the meibomian glands. These various treatments, however, can often take months before a treated patient notices any significant improvement.

Although the elimination of bacteria or anti-inflammatory effects of the antibiotics resulted in a temporary change, none of the known treatment methodologies have brought long-lasting relief to patients. Hoping to provide a form of sustainable relief to the ongoing symptoms associated with dry eye, with or without meibomian gland dysfunction, that are suffered by patients, a study was conducted by those skilled in the art to investigate the effects of dietary supplementation of a combination of flaxseed and fish oils on the tear film and the ocular surface. At the baseline, all patients in the study had a history of dry eye or symptoms of dry eyes. At the end of the study, the results did not achieve statistical significance, wherein the lipid composition of the samples collected from the omega-3 supplemented group was found to be very similar to that from the placebo group. Thus, the study concluded that dietary supplementation of flaxseed oil and omega-3 fatty acids for treating dry eye or meibomianitis showed no significant effect in meibum lipid composition or aqueous tear evaporation rate.

Consistent with the foregoing, in order to control or resolve the long term effects of dry eye or meibomianitis, the characteristics or nature of the oil that is produced by the meibomian glands must be normalized. Thus, what is needed are nutritional or dietary supplement compositions and treatment methodologies that effectively change the quality of the meibum lipid, thereby resulting in a meibum composition having a direct correlation to enhancing and improving the function and/or composition of the lipid layer of the tear.

SUMMARY AND OBJECTS OF THE INVENTION

In view of the foregoing, it is a primary object of the present invention to provide a nutritional or dietary supplement composition that effectively changes the quality of the meibum lipid resulting in a meibum composition that has a direct correlation to improving or increasing tear break up time, reducing tear osmolarity, and elevating omega-3 index, while eliminating or reducing the related symptoms of dry eye or meibomianitis.

It is a further object of the present invention to provide systems and methods for treating blepharitis by effectively changing the quality of the meibum lipid resulting in a meibum composition that improves or increases tear breakup time, reduces tear osmolarity, and elevates the omega-3 index, while eliminating or reducing the related symptoms.

It is a still further object of the present invention to provide a method of treating meibomianitis by effectively changing the quality of the meibum lipid resulting in a meibum composition that improves or increases tear breakup time, reduces tear osmolarity, and elevates the omega-3 index, while eliminating or reducing the related symptoms.

Additionally, it is an object of the present invention to provide a method for treating dry eye by administering an embodiment of a nutritional or dietary supplement composition as taught by the present invention.

It is a further object of the present invention to provide a method for changing the composition of the oil produced by any of the sebaceous gland found in the body from pro-inflammatory omega-6 to anti-inflammatory omega-3, whereby normalizing the oil production of the gland by way of administering an embodiment of a nutritional or dietary supplement composition as taught by the present invention.

It is also an object of the present invention to provide a method for treating acne by way of changing the composition of the oil produced by the sebaceous gland found in the skin from pro-inflammatory omega-6 to anti-inflammatory omega-3, whereby normalizing the oil production of the gland by way of administering an embodiment of a nutritional or dietary supplement composition as taught by the present invention.

It is a still further object of the present invention to provide a method for treating post surgical inflammation by preoperatively administering an embodiment of a nutritional or dietary supplement composition as taught by the present invention, whereby effecting a decrease in post surgical tissue inflammation.

Consistent with the foregoing objects, the present invention is directed to systems and methods for delivering a nutritional or dietary supplement composition to a patient suffering from symptoms associated with posterior blepharitis. Said systems and methods comprise the administration of a nutritional or dietary supplement composition formulated to effectively change the quality of the meibum lipid composition of the meibomian glands so as to improve or increase tear break up time, reduce tear osmolarity, and elevate the omega-3 index and, consequently, eliminate or reduce the related symptoms of dry eye or meibomianitis.

In an embodiment of the present invention, the present invention provides for methods for treating and preventing dry eye associated with meibomian gland inflammation or dysfunction by way of administering a nutritional or dietary supplement composition comprising an effective amount of omega-3 fatty acids. The supplementation may include an effective amount of omega-3 fatty acids comprising a daily dosage that includes between about 600 mg and about 5,000 mg.

The effective amount of omega-3 fatty acids may comprise an effective amount of eicosapentaenoic acid (EPA). In one embodiment of the present invention, the daily dosage of an effective amount of EPA may include an amount greater than 600 mg.

In yet another embodiment of the present invention, the effective amount of omega-3 fatty acids may comprise an effective amount of docosahexaenoic acid (DHA). The daily dosage of an effective amount of DHA may include an amount greater than 500 mg.

In certain embodiments of the present invention, an effective amount of omega-3 fatty acids may be delivered in a daily dosage that includes between about 2,000 mg and about 3,000 mg. This effective amount of omega-3 fatty acids may comprise an effective amount of eicosapentaenoic acid (EPA) and an effective amount of docosahexaenoic acid (DHA). Similarly, in one embodiment of the present invention, the daily dosage of an effective amount of EPA may include an amount between about 1,600 mg and about 2,500 mg and the daily dosage of an effective amount DHA may include an amount between about 500 mg and about 900 mg.

An additional amount of omega-3 fatty acids may also be included in the administered composition. These additional omega-3 fatty acids may include a daily dosage amount of between about 400 mg and about 700 mg. Furthermore, the nutritional or dietary supplement composition of the present invention may include an effective amount of Vitamin D (as D3). Such effective amount of Vitamin D may comprise a daily dosage amount between about 500 IU and about 2,000 IU. As contemplated herein, the administration of the dietary or nutritional supplement composition of the present invention to effectively change the quality of the meibum lipid composition of the meibomian glands may be delivered by means of softgel, tablet, liquids, granules, microgranules, powders, or any other delivery system deemed effective.

DETAILED DESCRIPTION OF THE PREFERRED EMBODIMENTS

It will be readily understood that the components of the present invention, as generally described herein, could be modified, arranged and designed in a wide variety of different formulas. Thus, the following more detailed description of the embodiments of the composition and systems and methods of the present invention is not intended to limit the scope of the invention. The scope of the invention is as broad as claimed herein.

As used herein, the term "effective amount" includes the amount of omega-3 fatty acids which is capable of effectively changing the quality of the meibum lipid concentration which has a direct correlation to improving the lipid layer of the tear, while eliminating or reducing the related symptoms of dry eye or meibomianitis.

As used herein, the terms "meibomiantis, meibomian gland dysfunction, posterior blepharitis, and blepharitis" are to be considered as synonyms.

The present invention provides for methods for treating and preventing dry eye associated with meibomian gland inflammation or dysfunction by way of administering a nutritional or dietary supplement composition comprising an effective amount of omega-3 fatty acids. The supplementation may include an effective amount of omega-3 fatty acids comprising a daily dosage that includes between about 600 mg and about 5,000 mg.

This effective amount of omega-3 fatty acids may comprise an effective amount of eicosapentaenoic acid (EPA). In one embodiment of the present invention, the daily dosage of an effective amount of EPA may include an amount greater than 600 mg.

In yet another embodiment of the present invention, the effective amount of omega-3 fatty acids may comprise an effective amount of docosahexaenoic acid (DHA). The daily dosage of an effective amount of DHA may include an amount greater than 500 mg.

In certain embodiments, the dietary or nutritional supplementation may include an effective amount of omega-3 fatty acids comprising a daily dosage including an effective amount between about 2,000 mg and about 3,000 mg. This effective amount of omega-3 fatty acids may be comprised of an effective amount of eicosapentaenoic acid (EPA) and an effective amount of docosahexaenoic acid (DHA). In an embodiment of the present invention, the daily dosage of an effective amount of EPA may include an amount between about 1,600 mg and about 2,500 mg and the daily dosage of an effective amount DHA may include an amount between about 500 mg and about 900 mg.

As appreciated by those skilled in the art, the dietary or nutritional supplement composition of the present invention includes omega-3 fatty acids that may comprise, for example, but not by way of limitation, the triglyceride form (natural oils), re-esterified triglyceride concentrates, the ethyl ester form, the free fatty acid form, the phospholipids form, or any other suitable form sufficient to effectively change the quality of the meibum lipid resulting in a meibum composition which has a direct correlation to improving the lipid layer of the tear, while eliminating or reducing the related symptoms of dry eye or meibomianitis. In certain embodiments of the present invention, the dietary or nutritional supplement composition administered for treating posterior blepharitis, meibomianitis, and/or for changing the quality of the meibum lipid concentration of inflamed or dysfunctional meibomian glands in order to improve or increase tear break up time, reduce tear osmolarity, and elevate the omega-3 index may comprise omega-3 fatty acids in the triglyceride form.

The effective amount of eicosapentaenoic acid (EPA) and/or an effective amount of docosahexaenoic acid (DHA) included in the dietary or nutritional supplement of the present invention may be obtained from known sources, such as for example, and not by way of limitation, fish, algae, squid, yeast, and vegetable sources. It is further recognized that Stearidonic Acid is a precursor to EPA and DHA and that consuming a product rich in Stearidonic Acid may be used to achieve the benefits as disclosed herein.

In selected embodiments of the nutritional or dietary supplement composition of the present invention, an effective amount of EPA/DHA may be administered in one or more softgel capsules containing an amount in the range of between about 800 mg and 1,250 mg and between about 250 mg and about 450 mg, respectively. For purposes of dosage, in certain embodiments of the present invention, the daily dosage amount may include an effective amount of EPA/DHA comprising the amounts of 840 mg and 280 mg, respectively.

In certain embodiments, this effective amount of EPA/DHA form may comprises a ratio of EPA/DHA of 3:1. Whereas, in selected embodiments, the ratio of EPA/DHA in each capsule may be in the range of between about 800 mg and 1,250 mg of EPA and between about 250 mg and 450 mg of DHA, whereby two capsules would comprise a daily effective dosage range.

An additional amount of omega-3 fatty acids may also be included in the administered composition. These additional omega-3 fatty acids may include a daily dosage amount of between about 400 mg and about 700 mg.

Furthermore, the nutritional or dietary supplement composition of the present invention may include an effective amount of Vitamin D (as D3). Such effective amount of Vitamin D may comprise a daily dosage amount of between about 500 IU and about 2,000 IU.

The following study was conducted based on the following parameters:

Objective:

To investigate and determine if subjects presenting with dry eye (compromised tear break up time) respond to the supplementation of omega-3 fatty acids in triglyceride form, as taught by the present invention, such that there is a quantitative change in the quality of the meibum lipid concentration that facilitates an impact in the reduction of tear osmolarity, while eliminating or reducing the symptoms of dry eye or meibomianitis.

Subjects:

A total of twenty (20) subjects, between the ages of 18-60 years of age inclusive, who voluntarily provided written informed consent and who were capable of complying with the study visit schedule, were enrolled.

Visits:

There were three (3) scheduled visits with an attending physician. The first visit included an initial base line analysis for inclusion in the study. The second visit involved a 4-week follow-up and the third visit was an 8-week follow-up.

Study Population:

The parameters of the study protocol for the "inclusion" of participants included the following conditions: (1) the participant must be of the age of 18 to 60 at the time of signing the informed consent; (2) must understand, be willing and able, and likely to fully comply with study procedures, visit schedule, and restrictions; and (3) have a diagnosis of dry eye disease based on a global clinical assessment by the attending clinician, patient complaint of dry eye symptoms, and compromised tear break up time.

The parameters of the study protocol for the "exclusion" of participants included the following conditions: (1) clinically significant eyelid deformity or eyelid movement disorder that is caused by conditions such as notch deformity, incomplete lid closure, entropion, ectropion, hordeola, or chalazia; (2) previous ocular disease leaving sequelae or requiring current topical eye therapy other than for DED, including, but not limited to: active corneal or conjunctival infection of the eye and ocular surface scarring; (3) active ocular or nasal allergy; (4) LASIK or PRK surgery that was performed within one (1) year of Visit 1 or at any time during the study; (5) ophthalmologic drop use within 2 hours of Visits 1, 2, or 3; (6) pregnancy or lactation at any time during the study; (7) abnormality of nasolacrimal drainage (by history); (8) previous Punctal plugs placement or cauterization; (9) started or changed the dose of chronic systemic medication known to affect tear production including, but not limited to antihistamines, antidepressants, diuretics, corticosteroids or immunomodulators within 30 days of Visit 1, 2, or 3

Study Design:

This is a single-center study of patients with signs and symptoms of dry eye undergoing nutritional therapy treatment with an amount of omega-3 fatty acids delivered in triglyceride form over the course of three (3) visits with approximately 4-week intervals between each visit.

The following clinical tests were performed at each visit: (1) Symptom Assessment in Dry Eye (SANDE) Questionnaire; (2) Tear Break Up Time analysis; and (3) tear osmolarity measurement.

The following clinical tests were performed at baseline and the 8-week visit: (1) Meibum Analysis and (2) RBC saturation analysis (HS Omega-3 Index).

Outcome:

Increase in omega-3 RBC and meibum composition had a direct correlation to the improvement of tear break up time, reduction in tear osmolarity, and elevation of omega-3 index from baseline. The study also demonstrated the new presence of omega-3 fatty acids within the meibum itself in seventeen (17) of the twenty (20) patients.

The following examples will illustrate several embodiments of the present invention in further detail. It will be readily understood that the nutritional or dietary supplement composition of the present invention, as generally described and illustrated in the Examples herein, could be synthesized in a variety of formulations and dosage forms. Thus, the following more detailed description of the embodiments of the methods, formulations and compositions of the present invention, as represented in the Examples are not intended to limit the scope of the invention, as claimed, but it is merely representative of various contemplated embodiments of the present invention.

Example I

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| Omega-3 fatty acids | 600 mg-5,000 mg |
|---|---|

In certain embodiments of the present invention, a method for treating posterior blepharitis in a patient comprises the step of administering an effective amount of the dietary or nutritional supplement composition as disclosed in Example I. Additionally, administering to a patient an effective amount of the dietary or nutritional supplement composition disclosed in Example I will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example II

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| Omega-3 fatty acids | 1,000 mg-3,000 mg |
|---|---|

In certain embodiments of the present invention, a method for treating posterior blepharitis in a patient comprises the step of administering an effective amount of the dietary or nutritional supplement composition as disclosed in Example II. Additionally, administering to a patient an effective amount of the dietary or nutritional supplement composition disclosed in Example II will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example III

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| omega-3 fatty acids | 2,000 mg-3,000 mg |
|---|---|

In certain embodiments of the present invention, a method for treating posterior blepharitis in a patient comprises the step of administering an effective amount of the dietary or nutritional supplement composition as disclosed in Example III. Additionally, administering to a patient an effective amount of the dietary or nutritional supplement composition disclosed in Example III will effectively change the quality of the meibum lipid composition of the meibomian glands thereby resulting in a meibum composition having a direct correlation to reducing tear break up time and elevating the omega-3 index, while eliminating or reducing the related symptoms of dry eye or meibomianitis. In certain embodiments, the omega-3 fatty acids comprise the triglyceride form.

Example IV

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| eicosapentaenoic acid (EPA) | ≥600 mg |
|---|---|
| docosahexaenoic acid (DHA) | ≥500 mg |

In certain embodiments of the present invention, a method for treating posterior blepharitis in a patient comprises the step of administering an effective amount of the dietary or nutritional supplement composition as disclosed in Example IV. Additionally, administering to a patient an effective amount of the dietary or nutritional supplement composition disclosed in Example IV will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example V

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| docosahexaenoic acid (DHA) | ≥500 mg |

In certain embodiments of the present invention, a method for treating posterior blepharitis in a patient comprises the step of administering an effective amount of the dietary or nutritional supplement composition as disclosed in Example V. Additionally, administering to a patient an effective amount of the dietary or nutritional supplement composition disclosed in Example V will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example VI

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | ≥600 mg |
| docosahexaenoic acid (DHA) | ≥500 mg |
| other omega-3 fatty acids | 400 mg-700 mg |

In certain embodiments of the present invention, a method for treating posterior blepharitis in a patient comprises the step of administering an effective amount of the dietary or nutritional supplement composition as disclosed in Example VI. Additionally, administering to a patient an effective amount of the dietary or nutritional supplement composition disclosed in Example VI will effectively change the quality of the meibum lipid composition of the meibomian glands thereby resulting in a meibum composition having a direct correlation to reducing tear break up time and elevating the omega-3 index, while eliminating or reducing the related symptoms of dry eye or meibomianitis. In certain embodiments, the omega-3 fatty acids comprise the triglyceride form.

Example VII

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | 1,600 mg-2,500 mg |
| docosahexaenoic acid (DHA) | 500 mg-900 mg |
| other omega-3 fatty acids | 400 mg-700 mg |

In certain embodiments of the present invention, a method for treating posterior blepharitis in a patient comprises the step of administering an effective amount of the dietary or nutritional supplement composition as disclosed in Example VII. Additionally, administering to a patient an effective amount of the dietary or nutritional supplement composition disclosed in Example VII will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example VIII

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | ≥600 mg |
| docosahexaenoic acid (DHA) | ≥500 mg |
| Vitamin D (as D3) | 500 IU-2,000 IU |

In certain embodiments of the present invention, a method for treating posterior blepharitis in a patient comprises the step of administering an effective amount of the dietary or nutritional supplement composition as disclosed in Example VIII. Additionally, administering to a patient an effective amount of the dietary or nutritional supplement composition disclosed in Example VIII will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example IX

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | 1,600 mg-2,500 mg |
| docosahexaenoic acid (DHA) | 500 mg-900 mg |
| Vitamin D (as D3) | 500 IU-2,000 IU |

In certain embodiments of the present invention, a method for treating posterior blepharitis in a patient comprises the step of administering an effective amount of the dietary or nutritional supplement composition as disclosed in Example IX. Additionally, administering to a patient an effective amount of the dietary or nutritional supplement composition disclosed in Example DC will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example X

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | ≥600 mg |
| docosahexaenoic acid (DHA) | ≥500 mg |
| other omega-3 fatty acids | 400 mg-700 mg |
| Vitamin D (as D3) | 500 IU-2,000 IU |

In certain embodiments of the present invention, a method for treating posterior blepharitis in a patient comprises the step of administering an effective amount of the dietary or nutritional supplement composition as disclosed in Example X. Additionally, administering to a patient an effective amount of the dietary or nutritional supplement composition disclosed in Example X will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example XI

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | 1,600 mg-2,500 mg |
| docosahexaenoic acid (DHA) | 500 mg-900 mg |
| other omega-3 fatty acids | 400 mg-700 mg |
| Vitamin D (as D3) | 500 IU-2,000 IU |

In certain embodiments of the present invention, a method for treating posterior blepharitis in a patient comprises the step of administering an effective amount of the dietary or nutritional supplement composition as disclosed in Example XI. Additionally, administering to a patient an effective amount of the dietary or nutritional supplement composition disclosed in Example XI will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example XII

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | 1,650 mg-1,750 mg |
| docosahexaenoic acid (DHA) | 500 mg-600 mg |
| other omega-3 fatty acids | 400 mg-500 mg |
| Vitamin D (as D3) | 600 IU-800 IU |

In certain embodiments of the present invention, a method for treating posterior blepharitis in a patient comprises the step of administering an effective amount of the dietary or nutritional supplement composition as disclosed in Example XII. Additionally, administering to a patient an effective amount of the dietary or nutritional supplement composition disclosed in Example XII will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Example XIII

A daily dosage formulation of an embodiment of the nutritional or dietary supplement composition of the present invention administered for effectively changing the quality of the meibum lipid composition resulting in improved or increased tear break up time, reduced tear osmolarity, and elevation of omega-3 index is set forth as comprising:

| | |
|---|---|
| eicosapentaenoic acid (EPA) | 1,680 mg |
| docosahexaenoic acid (DHA) | 560 mg |
| other omega-3 fatty acids | 428 mg |
| Vitamin D (as D3) | 334 IU |

In certain embodiments of the present invention, a method for treating posterior blepharitis in a patient comprises the step of administering an effective amount of the dietary or nutritional supplement composition as disclosed in Example XIII. Additionally, administering to a patient an effective amount of the dietary or nutritional supplement composition disclosed in Example XIII will effectively change the quality of the meibum lipid composition of the meibomian glands thereby resulting in a meibum composition having a direct correlation to increasing tear breakup time and elevating the omega-3 index, while eliminating or reducing the related symptoms of dry eye or meibomianitis. In certain embodiments, the omega-3 fatty acids comprise the triglyceride form.

Consistent with the foregoing, certain embodiments of the present invention provide methods of administering a nutritional or dietary supplement composition to effectively change the quality of the meibum lipid composition of the meibomian glands thereby resulting in a meibum composition which has a direct correlation to improving or increasing tear break up time, reducing tear osmolarity, and elevating the omega-3 index, while eliminating or reducing the related symptoms of dry eye or meibomianitis. The present invention also provides methods for treating blepharitis by effectively changing the quality of the meibum lipid resulting in a meibum composition thereby increasing tear breakup time and elevated omega-3 index, while eliminating or reducing the related symptoms. Certain embodiments of the present invention further provide methods for treating meibomianitis by effectively changing the quality of the meibum lipid resulting in a meibum composition that improves or increases tear breakup time, reduces tear osmolarity, and elevates the omega-3 index, while eliminating or reducing the related symptoms. Moreover, embodiments of the present invention provide methods for changing the composition of the oil produced by any of the sebaceous gland found in the body from pro-inflammatory omega-6 to anti-inflammatory omega-3, whereby normalizing the oil production of the gland by way of administering an embodiment of a nutritional or dietary supplement composition as taught and disclosed herein. Embodiments of the present invention also teach a method for treating acne by way of changing the composition of the oil produced by the sebaceous gland found in the skin from pro-inflammatory omega-6 to anti-inflammatory omega-3, whereby normalizing the oil production of the gland by way of administering an embodiment of a nutritional or dietary supplement composition as taught by the present invention. Further, certain embodiments of the present invention provide a method for treating post surgical inflammation by preoperatively administering an embodiment of a nutritional or dietary supplement composition as taught by the present invention, whereby effecting a decrease in post surgical tissue inflammation.

The present invention may be embodied in other specific forms without departing from its fundamental functions or essential characteristics. The described embodiments are to be considered in all respects only as illustrative, and not restrictive. All changes which come within the meaning and range of equivalency of the illustrative embodiments are to be embraced within their scope.

What is claimed and desired to be secured by United States Letters Patent is:

1. A composition consisting of a single Fatty acid for improving the quality of the meibum composition of inflamed or dysfunctional meibomian glands, wherein said fatty acid consists of omega-3 fatty acids in the triglyceride form in an amount greater than 600 mg.

2. The composition consisting of a single fatty acid for improving the quality of the meibum composition of inflamed or dysfunctional meibomian glands as defined in claim 1, wherein said omega-3 fatty acids comprises eicosapentaenoic acid (EPA).

3. The composition consisting of a single fatty acid for improving the quality of the meibum composition of inflamed or dysfunctional meibomian glands as defined in claim 2, wherein said effective amount of EPA comprises an amount between 1,600 mg and 2,500 mg.

4. The composition consisting of a single fatty acid for improving the quality of the meibum composition of inflamed or dysfunctional meibomian glands as defined in claim 2, wherein said effective amount of EPA comprises an amount between 1,600 mg and 1,800 mg.

5. The composition consisting of a single fatty acid for improving the quality of the meibum composition of inflamed or dysfunctional meibomian glands as defined in claim 2, wherein said effective amount of EPA comprises 1,680 mg.

6. The composition consisting of a single fatty acid for improving the quality of the meibum composition of inflamed or dysfunctional meibomian glands as defined in claim 2, wherein said effective amount of EPA comprises esterified triglyceride form.

7. The composition consisting of a single fatty acid for improving the quality of the meibum composition of inflamed or dysfunctional meibomian glands as defined in claim 2, wherein said effective amount of EPA comprises re-esterified triglyceride form.

8. The composition consisting of a single fatty acid for improving the quality of the meibum composition of inflamed or dysfunctional meibomian glands as defined in claim 2, further comprising an effective amount of docosahexaenoic acid (DHA), wherein said effective amount of DHA comprises an amount greater than 500 mg.

9. The composition consisting of a single fatty acid for improving the quality of the meibum composition of inflamed or dysfunctional meibomian glands as defined in claim 8, wherein said EPA and said DHA are in a 3:1 ratio.

10. The composition consisting of a single fatty acid for improving the quality of the meibum composition of inflamed or dysfunctional meibomian glands as defined in claim 8, wherein said effective amount of DHA comprises an amount between 500 mg and 900 mg.

11. The composition consisting of a single fatty acid for improving the quality of the meibum composition of inflamed or dysfunctional meibomian glands as defined in claim 8, wherein said effective amount of DHA comprises 560 mg.

12. The composition consisting of a single fatty acid for improving the quality of the meibum composition of inflamed or dysfunctional meibomian glands as defined in claim 8, wherein said DHA comprises the triglyceride form.

13. The composition consisting of a single fatty acid for improving the quality of the meibum composition of inflamed or dysfunctional meibomian glands as defined in claim 8, wherein said effective amount of DHA comprises esterified triglyceride form.

14. The composition consisting of a singer fatty acid for improving the quality of the meibum composition of inflamed or dysfunctional meibomian glands as defined in claim 8, wherein said effective amount of DHA comprises re-esterified triglyceride form.

15. A composition consisting of a single fatty acid for improving the quality of the meibum composition of inflamed or dysfunctional meibomian glands as defined in claim 1, wherein said composition further comprises between 500 IU and 2,000 IU of Vitamin D.

16. The composition consisting of a single fatty acid for improving the quality of the meibum composition of inflamed or dysfunctional meibomian glands as defined in claim 15, wherein said Vitamin D comprises between 600 IU and 800 IU.

17. A composition consisting of a single fatty acid for improving the quality of the meibum composition of inflamed or dysfunctional meibomian glands, said composition consisting of:
    an effective amount of omega-3 fatty acids in the triglyceride form, wherein said omega-3 fatty acids include eicosapentaenoic acid (EPA) in an amount greater than 600 mg; and
    an effective amount of vitamin D comprising between 600 IU and 800 IU.

18. The composition consisting of a single fatty acid for improving the quality of the meibum composition of inflamed or dysfunctional meibomian glands as defined in claim 17, further comprising an effective amount of docosahexaenoic acid (DHIA), wherein said effective amount of DHA comprises an amount greater than 500 mg.

19. The composition consisting of a single fatty acid for improving the quality of the meibum composition of inflamed or dysfunctional meibomian glands as defined in claim 17, wherein said effective amount of DHA comprises the triglyceride form.

20. The composition consisting of a single fatty acid for improving the quality of the meibum composition of inflamed or dysfunctional meibomian glands as defined in claim 18, wherein said EPA and said DHA are in a 3:1 ratio.

* * * * *

UNITED STATES PATENT AND TRADEMARK OFFICE
CERTIFICATE OF CORRECTION

| | | |
|---|---|---|
| PATENT NO. | : 9,115,078 B2 | Page 1 of 1 |
| APPLICATION NO. | : 13/507673 | |
| DATED | : August 25, 2015 | |
| INVENTOR(S) | : Smith et al. | |

It is certified that error appears in the above-identified patent and that said Letters Patent is hereby corrected as shown below:

In the specification

Column 10, line 61, delete "DC" and insert therefore -- IX --.

Column 13, line 31, delete "Fatty" and insert therefore -- fatty --.

In the claims

Column 14, line 26, claim 14 delete "singer" and insert therefore -- single --.

Column 14, line 55, claim 18 delete "DHIA" and insert therefore -- DHA --.

Column 14, line 59, claim 19 delete "17" and insert therefore -- 18 --.

Signed and Sealed this
Twenty-fourth Day of May, 2016

Michelle K. Lee
*Director of the United States Patent and Trademark Office*